United States Patent

Gupte et al.

[11] Patent Number: 6,087,099
[45] Date of Patent: Jul. 11, 2000

[54] METHOD FOR SEQUENCING BOTH STRANDS OF A DOUBLE STRANDED DNA IN A SINGLE SEQUENCING REACTION

[75] Inventors: Jamila Gupte, Layton; Arnold Oliphant, Erda, both of Utah

[73] Assignee: Myriad Genetics, Inc., Salt Lake City, Utah

[21] Appl. No.: 08/925,277

[22] Filed: Sep. 8, 1997

[51] Int. Cl.[7] .............................. C12P 19/34; C07H 21/04
[52] U.S. Cl. ........................ 435/6; 435/91.2; 536/24.3; 536/24.33; 536/26.6
[58] Field of Search ........................ 536/24.33, 24.3, 536/26.6; 435/91.2, 6

[56] References Cited

U.S. PATENT DOCUMENTS

5,411,875   5/1995   Jones ........................................ 435/91.2

OTHER PUBLICATIONS

Chadwick, RB, Conrad, MP, McGinnis, MD, JohnstonDow, L, Spurgeon, SL and Kronick, MN (1996). "Heterozygote and Mutation Detection by Direct Automated Fluorescent DNA Sequencing Using a Mutant Taq DNA Polymerase", *BioTechniques* 20:676–683.

Choi, T–J, Wagner, JD and Jackson, AO (1994). "Sequence Analysis of the Trailer Region of Sonchus Yellow Net Virus Genomic RNA", *Virology* 202:33–40.

Jones, DH (1995). "Panhandle PCR", *PCR Methods and Applications* 4:S195–S201.

Jones, DH and Winistorfer, SC (1992). "Sequence specific generation of a DNA panhandle permits OCR amplification of unknown flanking DNA", *Nucleic Acids Research* 20:595–600.

Jones, DH and Winistorfer, SC (1993). "Genome Walking with 2–to 4–kb Steps Using Panhandle PCR", *PCR Methods and Applications* 2:197–203.

Ju, J., Ruan, C., Fuller, CW, Glazer, AN and Mathies, RA (1995). "Fluorescence energy transfer dye–labeled primers for DNA sequencing and analysis", *Proc. Natl. Acad. Sci. USA* 92:4347–4351.

Wetzel, T., Dietzgen, RG and Dale, JL (1994). "Genomic Organization of Lettuce Necrotic Yellows Rhabdovirus", *Virology* 200:401–412.

*Primary Examiner*—Ardin H. Marschel
*Assistant Examiner*—Joyce Tung
*Attorney, Agent, or Firm*—Rothwell, Figg, Ernst & Kurz PC

[57] ABSTRACT

A method is presented which uses a unique opposite strand joining strategy during PCR of an original DNA to generate a product which, when sequenced with a single sequencing primer yields the sequence of both strands of the original DNA. The PCR primers include 1) a modified oligomer corresponding to the 5' end of a first strand of the DNA to be amplified wherein said modified oligomer includes the reverse complementary sequence to a sequence within said first strand of DNA and a specific PCR priming sequence which will specifically hybridize to a portion of the DNA to be amplified and 2) a second oligomer corresponding to the 5' end of the second strand of the DNA to be amplified and which contains the priming sequence for the second strand of the DNA and will specifically hybridize to a portion of the DNA to be amplified. During PCR an intermediate product is formed where one end of one strand loops around to hybridize to its complement on the same strand. This results in a hairpin structure which elongates using its own strand as a template to form a double sized product that contains the sequence of both original strands. Upon denaturation this yields single strands with the single strands having the sequence of both of the original strands included in tandem. Sequencing these single strands using a single primer, e.g., a primer complementary to the second oligomer, yields the sequences of both strands of the DNA of interest.

6 Claims, 3 Drawing Sheets

```
19R,5' AGGAAACAGCTATGACCATTGATCCTCATTATCATGGAAAATTTGT 3' SEQ ID NO:1
       |-------M13R--------||-----------G2'-----------|
```

```
19F,5' GTTTTCCCAGTCACGACGGTCATTCTTCCTGTGCTCTTTTGT 3' SEQ ID NO:2
       |--------M13F------||----------G1----------|
```

```
19XP,5' CAGCGATTCGTCATTCTTCCTGTGCTCTTTTGT 3' SEQ ID NO:3
        |---C'---||---------G1----------|
```

```
5'...tcctctGTCATTCTTCCTGTGCTCTTTTGTGAATCGCTGacctct...3'SEQ ID NO:4
      |------------G1------------||---C----|
```

19R,5' AGGAAACAGCTATGACCATTGATCCTCATTATCATGGAAAATTTGT 3' SEQ ID NO:1
       |-------M13R'--------||-----------G2'------------|

FIG. 1A 19F,5'  GTTTTCCCAGTCACGACGGTCATTCTTCCTGTGCTCTTTTGT 3' SEQ ID NO:2
        |--------M13F------||----------G1----------|

FIG. 1B

19XF,5' CAGCGATTCGTCATTCTTCCTGTGCTCTTTTGT 3' SEQ ID NO:3
        |---C'----||----------G1-----------|

FIG. 1C

5'...tcctctGTCATTCTTCCTGTGCTCTTTTGTGAATCGCTGacctct...3' SEQ ID NO:4
     |------------G1-----------||----C----|

FIG. 1D

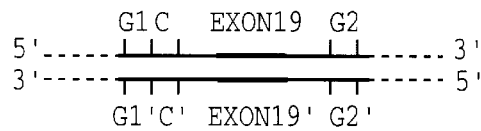
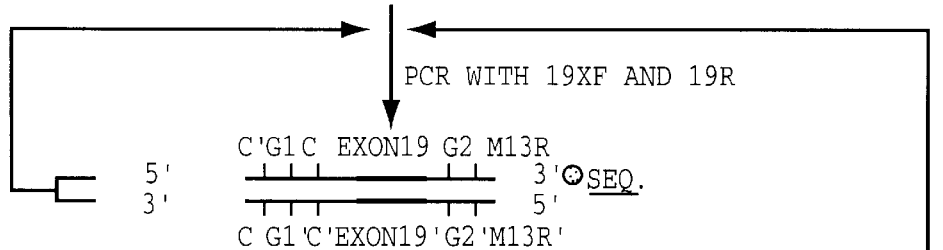
FIG. 2A
FIG. 2B
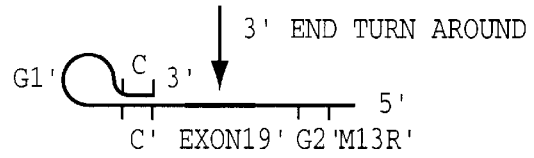
FIG. 2C
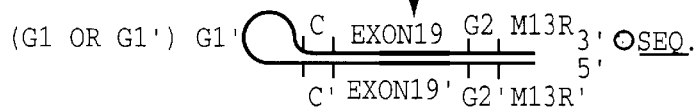
FIG. 2D
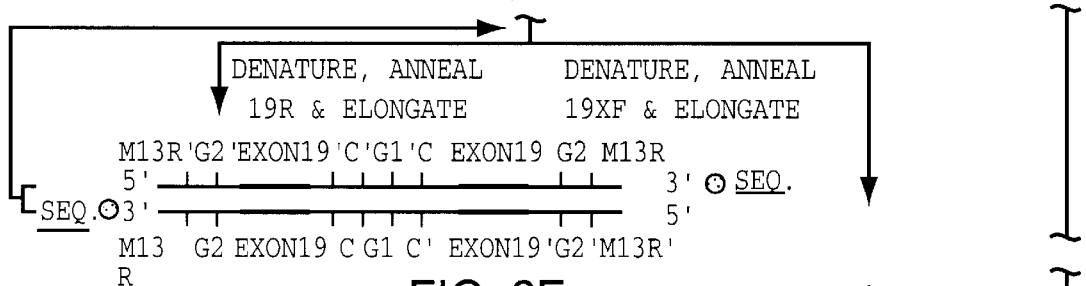
FIG. 2E
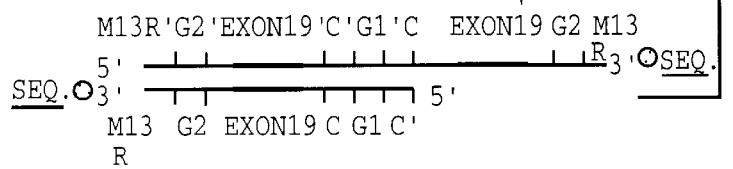
FIG. 2F

METHOD FOR SEQUENCING BOTH STRANDS OF A DOUBLE STRANDED DNA IN A SINGLE SEQUENCING REACTION

BACKGROUND OF THE INVENTION

Sequencing of nucleic acids is an extremely important and widely used technique. It is used for a variety of purposes. One such purpose is to identify whether mutations within genes of known sequence are present in a sample of DNA taken from a person. This is especially important in diagnosing whether the person may have a disease which is known to be associated with specific mutations in the gene being analyzed. When this type of testing is performed, it is common to sequence both strands of DNA to minimize any errors which may occur in the sequencing. To date, when sequencing both strands by the Sanger dideoxy method there has been a requirement to use one primer to sequence the sense strand and a second primer to sequence the antisense strand of the double-stranded DNA. The two strands have been sequenced in separate sets of reactions. The present invention is a technique by which both strands of DNA are sequenced in a single set of reactions using only a single primer. This method allows one to use fewer reactions for obtaining the data. This is especially important for laboratories which will be processing many samples. The use of fewer reactions will decrease the cost of analysis.

DNA sequencing methods were developed during the 1970s by Maxam and Gilbert (1977) and by Sanger (1977). The Sanger method which uses dideoxy nucleotides to terminate newly synthesized DNA strands is most commonly used and has been adapted such that it can be used with fluorescent markers rather than radioactivity. One variation is a technique called cycle sequencing in which DNA sequencing is combined with polymerase chain reaction (PCR). Chadwick et al. (1996) teach a variation of cycle sequencing in which a mutant Taq DNA polymerase is utilized.

The polymerase chain reaction itself is only one of a number of different methods now available for amplifying nucleic acids. Some of the other methods include ligase chain reaction (Wu and Wallace, 1989), Strand Displacement Amplification (SDA) (Walker, U.S. Pat. No. 5,455,166 (1995); Walker et al., 1992), thermophilic SDA (Spargo et al., 1996), and 3SR or NASBA (Compton, 1991; Fahy et al., 1991).

The instant invention is a method of using a specially designed oligomer which contains a reverse complement sequence along with a standard primer during PCR. This generates a double stranded DNA product such that when it is denatured one end of the resulting single stranded DNA loops around to form an intrastrand stem-loop structure. This structure is then elongated thereby producing a double-stranded DNA but wherein the two strands are joined by a loop. This method is referred to as opposite strand joining PCR. When denatured this product forms a single-stranded DNA which contains both strands of the original DNA. When this resulting single-stranded DNA is sequenced it yields the sequence of both strands of the original double-stranded DNA.

A similar stem-loop DNA structure was used as a template for PCR amplification by Jones et al. (1992). The Jones et al. reference describes a "panhandle PCR" method. This technique introduced a self-complementary portion into the target DNA strand by ligation. The goal of panhandle PCR is to amplify unknown sequence by generating a stem loop template structure for PCR whereas one of the goals of opposite strand joining PCR is to amplify known sequence by generating a stem-loop structure during PCR and then sequencing both strands of the longer product in one sequencing reaction. Another use for opposite strand joining PCR is in denaturing gradient gel electrophoresis techniques wherein the use of this technique can form a covalently bonded hairpin loop which can replace the use of a GC clamp. Yet another use for opposite strand joining PCR is simply the use of the method effectively to join together the two strands of any double stranded DNA into a single strand of DNA for any desired purpose.

SUMMARY OF THE INVENTION

A method is presented which uses a unique opposite strand joining strategy during PCR of an original DNA to generate a product which, when sequenced with a single sequencing primer yields the sequence of both strands of the original DNA. The PCR primers include 1) a modified oligomer corresponding to the 5' end of a first strand of the DNA to be amplified wherein said modified oligomer includes the reverse complementary sequence to a sequence within said first strand of DNA and a specific PCR priming sequence which will specifically hybridize to a portion of the DNA to be amplified and 2) a second oligomer corresponding to the 5' end of the second strand of the DNA to be amplified and which contains the priming sequence for the second strand of the DNA and will specifically hybridize to a portion of the DNA to be amplified. During PCR an intermediate product is formed where one end of one strand loops around to hybridize to its complement on the same strand. This results in a hairpin structure which elongates using its own strand as a template to form a double sized product that contains the sequence of both original strands. Upon denaturation this yields a single strand having the sequence of both of the original strands included in tandem. Sequencing these single strands using a single primer, e.g., a primer complementary to the second oligomer, yields the sequences of both strands of the DNA of interest.

BRIEF DESCRIPTION OF THE DRAWINGS

FIGS. 1A–1D show the primer design used in the Example. FIG. 1A shows the sequence of primer 19R which consists of the −28M13 reverse DET primer sequence (shown in bold) which is 5' to the gene specific sequence G2'. FIG. 1B shows the sequence of primer 19F which consists of the −40M13 forward DET sequence (shown in bold) which is 5' to the gene specific sequence G1. FIG. 1C shows the sequence of the opposite strand joining primer 19XF which consists of a short reverse complemented genomic sequence C' (shown in bold) which is 5' to the gene specific sequence G1 used in primer 19F. FIG. 1D shows the genomic sequence in the region of the opposite strand joining primer. The gene specific sequence G1 (shown in nonbolded upper case letters) used in both the 19F and 19XF primers is 5' of sequence C (shown in bold upper case letters). It is this genomic region C which is reverse complemented (and therefore called C') and placed 5' to the gene specific sequence G1 in the opposite strand joining primer 19XF.

FIGS. 2A–2F illustrate the opposite strand joining strategy. Throughout these figures, all the strands labeled •SEQ are substrates for dye primer sequencing.

FIG. 2A shows genomic DNA in the region of exon 19. This is shown as four sections on each strand with one strand having G1, C, the exon 19 containing region, and G2 and the opposite strand being designated with primes, e.g., G1', C', etc. Region C is the portion which is complementary to a portion of primer 19XF and which will hybridize with the appended primer so that there is intrastrand hybridization forming a loop and a double-stranded region of DNA. The exon 19 region is the region of interest to be sequenced.

FIG. 2B shows the product obtained when the DNA shown in FIG. 2A is subjected to PCR with primers 19XF and 19R. The major amplified product is similar to the DNA of FIG. 2A but has had a C'/C tail added at one end and an M13R/M13R' tail added at the other end.

FIG. 2C shows the exon 19' strand of FIG. 2B following denaturation. This illustrates that intrastrand binding occurs forming a loop with the C tail hybridizing to the C' portion of the strand. This product is a substrate for dye terminator sequencing in the absence of primer.

FIG. 2D illustrates the product formed after elongating the DNA shown in FIG. 2C. The product, which upon denaturation is a single-stranded molecule, contains both strands of exon 19, i.e., it contains both exon 19 and exon 19' in a tandem arrangement (separated by C, G1' and C').

FIG. 2E illustrates the product formed when the DNA of FIG. 2D undergoes another cycle of PCR using primer 19R. Note that the DNA shown in FIG. 2E is palindromic except for the very central G1/G1' region and sequencing both strands yields the identical sequence except for the G1/G1' region (which is not of interest). G1 and G1' are complementary and are of equal length and therefore the sequence obtained from both strands using a single primer is identical throughout except for the central G1/G1' section which will not interfere with the reading of the rest of the sequence. The fill length products formed and shown in FIG. 2E can then be used in further rounds of PCR using primer 19R.

FIG. 2F illustrates the products formed when the DNA of FIG. 2D undergoes another cycle of PCR using primers 19XF and 19R. The product shown is a result of primer 19XF priming this cycle on the FIG. 2D DNA. Each strand of this product can reenter the cycle of steps at step A (short strand) or step D (long strand).

FIG. 3A shows the sequence of exon 19' of the products B, D, E and F (shown in FIG. 2) amplified by the primers 19XF and 19R for which sequencing the –28M13 reverse primer was used.

FIG. 3B shows the sequence of exon 19 of the products B, D, E and F (shown in FIG. 2) amplified by the primers 19XF and 19R for which sequencing the –28M13 reverse primer was used.

FIG. 3C shows the sequence of exon 19' of the product amplified by the standard primers 19F and 19R gene for which sequencing the –28M13 reverse primer was used.

FIG. 3D shows the sequence of exon 19 of the product amplified by the standard primers 19F and 19R for which sequencing the –40M13 forward primer was used.

DESCRIPTION OF THE INVENTION

Figure 3A:
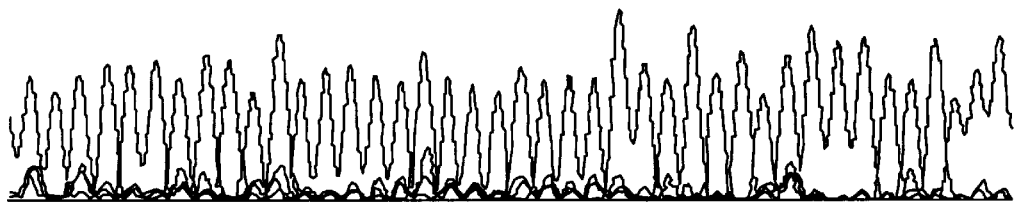
FIGS. 3A–3D show the sequence comparison of both strands of the BRCA1 exon 19 obtained from a single sequencing lane.

The present invention is directed to sequencing both strands of a double-stranded DNA molecule by using only a single set of labeled primers rather than using two sets of labeled primers as is done conventionally. The ability to sequence both strands using a single set of reactions is more efficient and less expensive. The method is especially appropriate for sequencing both strands of shorter pieces of DNA such that one strand of a DNA of double length could be sequenced in a single sequencing run by conventional methods.

The present invention is also especially suitable for use in clinical laboratories which will be sequencing large numbers of samples of genes of known sequence to determine whether the samples contain mutations. As an example, a diagnostic test for breast cancer (BRACAnalysis™) involves complete PCR and sequencing of the coding sequences and proximal introns of both alleles of a patient's BRCA1 and BRCA2 genes in order to find any deleterious mutations. To ensure high quality and consistency, the diagnostic test is completely automated. A total of 35 amplicons for BRCA1 and 47 amplicons for BRCA2 are sequenced. The PCR products sequenced during the standard BRACAnalysis™ are amplified with 5' M13 tailed gene specific primers. Following amplification, the products contain the M13 tail sequences at their ends. During sequencing both strands of the amplified products are sequenced in two separate reactions. The sequencing reactions are ethanol precipitated and resolved in two separate lanes on an Applied Biosystems 377 sequencing gel. The sequences obtained are analyzed for the presence of mutations and polymorphisms.

The instant invention involves a novel concept to sequence both strands of the amplified products in one sequencing reaction. The sequence obtained for both the DNA strands is present in a single lane of a sequencing gel. The Example below, which is not intended to limit the invention in any manner, describes use of this method for exon 19 in the BRCA1 gene. The tailed genomic primer 19R (see FIG. 1), developed for the standard BRACAnalysis™ test, in combination with the unique opposite strand joining primer 19XF is used for PCR. During PCR an intermediate turnaround strand is formed where the 3' end loops around and hybridizes to a complementary region on the same strand thus generating a stem loop structure. Elongation of this stem loop structure at the 3' end results in the formation of a longer product which contains the sequence of both strands. In a complex multiamplicon test such as BRACAnalysis™, application of this technique to each suitable amplicon will substantially reduce the number of sequencing reactions and the number of sequencing gel lanes used, making the test more cost efficient.

The method disclosed here is designated "opposite strand joining PCR". It uses an opposite strand joining primer during PCR to generate a turnaround structure resulting in the formation of a double size DNA strand (FIGS. 2C and 2D). Combination of the opposite strand joining primer (19XF in FIG. 1C) and the 19R primer (FIG. 1A) was used during PCR. PCR with these two primers results in the formation of a double-stranded intermediate product of which one of the strands containing the M13 tail at the 3' end can be sequenced using the –28M13 reverse sequencing primer (FIG. 2B). The 3' end of the other strand can turn around to form a stem loop structure by intra-strand annealing where the 3' end hybridizes to the complementary sequence on the same strand (FIG. 2C). This 3' end can then be used as a primer for the same strand and elongate to form the double size product (FIG. 2D). During the next PCR cycle, this longer product denatures and anneals with the 19XF and 19R primers which elongate. This results in the formation of products as shown in FIGS. 2E and 2F. These products are templates for primer annealing and elongation during the next PCR cycles.

To verify the formation of the turnaround intermediate structure in FIG. 2C, dye terminator sequencing was performed for the products amplified by the primers 19XF and 19R. The turned around 3' end (FIG. 2C) acts as a primer and elongates using the same strand as a template during dye terminator sequencing. Sequence of only one strand was observed by dye terminator sequencing (data not shown). Thus, PCR amplification with an opposite strand joining primer enables dye terminator sequencing to be carried out without a primer.

The technique of opposite strand joining PCR is useful for modifying denaturing gradient gel electrophoresis (DGGE), a technique used for mutation screening. Single base changes in the DNA have been detected by DGGE using a GC clamp attached to one end of the amplified product (Fischer et al., 1983; Myers et al., 1985a; Myers et al., 1985b). Addition of a GC clamp at the end of the PCR product using a modified primer creates a high melting temperature region making it possible to detect base changes in the rest of the strand. The GC clamp can be replaced by a covalently bonded hairpin loop by designing an opposite strand joining primer. The region of interest is amplified using the combination of the opposite strand joining primer designed at one end and a conventional primer at the other end of the region.

Definitions

A "primer" is an oligomer which will hybridize to a strand of nucleic acid and which can be extended or elongated by the addition of nucleotides to form a nucleic acid strand of complementary sequence to the strand of nucleic acid to which the primer is hybridized. One example of such a reaction is the polymerase chain reaction in which two primers are used wherein one primer is complementary to the 5' end of nucleic acid to be amplified and a second primer is complementary to the 3' end of nucleic acid to be amplified and further wherein one primer is complementary to the sense strand and the other primer is complementary to the antisense strand. Another example is a sequencing reaction wherein the DNA to be sequenced is made single-stranded and a primer is added which primer is complementary to a portion of one of the single strands of DNA and is elongated.

A "single primer" means a primer comprising a single nucleotide sequence. The phrase "single primer" may encompass more than only one primer. It encompasses, e.g., four distinct primers which all have identical nucleotide sequences but which are labeled with four distinct markers such as four different fluors wherein each primer molecule comprises one of the four fluors. Each of these four primers may be used separately in sequencing reactions, yet they are together considered to be a single primer. Alternatively, a single primer may in fact represent only one primer which is identical in all cases, such as will occur when sequencing using a radioactively labeled primer or radioactively labeled dNTPs or when performing dye terminator sequencing, but the definition is not so limited for purposes of the present disclosure.

A "single set of sequencing reactions" refers to the reactions necessary to sequence a single strand of DNA. Commonly a single set of sequencing reactions will consist of four separate reactions which later are either run on four lanes of a gel if a radioactive label is used or are mixed together and run on a single lane of a gel if fluorescent labels are used.

A "reverse complementary sequence of nucleotides" refers to a sequence of nucleotides within a strand of DNA which is complementary to another sequence of nucleotides within the same strand of DNA but in the reverse order such that when the single strand folds back upon itself the reverse complementary sequence of nucleotides can hybridize to its complementary sequence within the same strand thereby yielding a hairpin structure.

"Effectively to join" together two strands of a double-stranded DNA into a single-stranded DNA means to use a method which does not actually join the two existing strands of double-stranded DNA together but which has the same effect as so doing for a portion of the double-stranded DNA. The original double-stranded DNA is amplified and the newly formed DNA undergoes steps to yield a single-stranded DNA which includes the same sequences as found in the two strands of a portion of the amplified region of the double-stranded DNA. The result is that, although the two strands of the original double-stranded DNA are not themselves joined together, the effect is the same as having done so for a portion of the original double-stranded DNA.

EXAMPLE

A. Primer Design

The primers 19F and 19R (see FIGS. 1A and 1B) are the primers for exon 19 of the BRCA1 gene used in the standard BRACAnalysis™ diagnostic assay. These primers contain the gene specific region and the −40M13 forward or −28M13 reverse DYEnamic energy transfer (DET) primer sequence from Amersham Life Science at its 5' end.

The opposite strand joining primer, 19XF (FIG. 1C), for exon 19 was designed as follows. This primer contains the same gene specific sequence G1 as the 19F primer but the sequence at the 5' end contains a 9 basepair reverse complemented genomic sequence (C'). The genomic sequence C which corresponds to C' is present 3' to the 19F gene specific sequence G1 in the genomic DNA (FIG. 1D and FIG. 2A).

B. Polymerase Chain Reaction

Human genomic DNA was amplified by PCR using the primer 19R in combination with either primer 19F (for the linear product) or 19XF (for the turnaround product). The reactions were carried out in a total volume of 9 $\mu$L and contained 20 ng DNA, 0.2 mM each dNTP, 0.5 units Amplitaq Gold DNA polymerase (from Perkin-Elmer), 10 mM Tris pH8.3, 50 mM KCl, 1 mM EDTA, 6.5 mM MgCl$_2$, 10% sucrose and 0.01% Tween 20, 0.1 $\mu$M of primer 19R and either 0.1 $\mu$M of primer 19F or 0.4 $\mu$M primer 19XF, respectively. The reactions were layered with oil and then cycled in the DNA Engine Thermal cycler at 94° C. for 10 minutes followed by 36 cycles of 96° C. for 20 seconds, 62° C. for 30 seconds and 72° C. for 60 seconds. This was followed by 1 cycle at 72° C. for 60 seconds.

C. Sequencing

Dye primer sequencing reactions were carried out with half volume of 1:10 diluted PCR products, 0.2 $\mu$M dideoxynucleotide/45$\mu$M deoxynucleotide mix, 80 mM Tris pH 9.5, 2% sucrose, 0.05% Triton X, 1 mM EDTA, 5 mM MgSO$_4$, 0.075 units Taq FS polymerase (Kalman et al., 1995; Tabor et al., 1995) and 0.04 $\mu$M −40M13 forward or −28M13 reverse DET primers (Ju et al., 1995a; Ju et al., 1995b). The reactions were layered with oil and then cycled in the DNA Engine Thermal cycler for 32 cycles at 96° C. for 20 seconds, 56° C. for 30 seconds and 72° C. for 60 seconds, followed by one cycle at 72° C. for 60 seconds.

The product amplified by the primers 19F and 19R was sequenced in both directions using the −40M13 forward and the −28M13 reverse sequencing primers. The products created by the primers 19XF and 19R were sequenced using the −28M13 reverse sequencing primer. The four forward (or reverse) reactions were pooled and ethanol precipitated. The precipitate was resuspended in 50% formamide, 50 mM EDTA, denatured and loaded on an Applied Biosystems 377 sequencing gel.

D. Results

FIGS. 2A–2F illustrate opposite strand joining PCR for exon 19 of BRCA1 where one strand of the double stranded product shown in FIG. 2B, the turnaround product shown in FIG. 2D and both strands of the products shown in FIGS. 2E and 2F are substrates for dye primer sequencing using the −28M13 reverse sequencing primer. The two strands of exon 19 (strands 19 and 19') are present on two different strands in the genomic DNA (FIG. 2A). When genomic DNA is amplified in the conventional manner using primers 19F and 19R, a double-stranded product is generated in which one strand contains the exon 19 strand and the opposite strand contains the exon 19' strand. In contrast to this conventional result, opposite strand joining PCR generates products shown in FIGS. 2D and 2E in which the original exon 19 and exon 19' strands are both contained within a single strand of DNA. The longer strand of the product shown in FIG. 2F also contains both the exon 19 and exon 19' strands. The sequence of exon 19 and exon 19' in these products can be obtained by using only one sequencing primer since the 19R primer has the −28M13 sequence at its 5' end whereas the 19XF primer has no M13 tail.

Figure 3B:
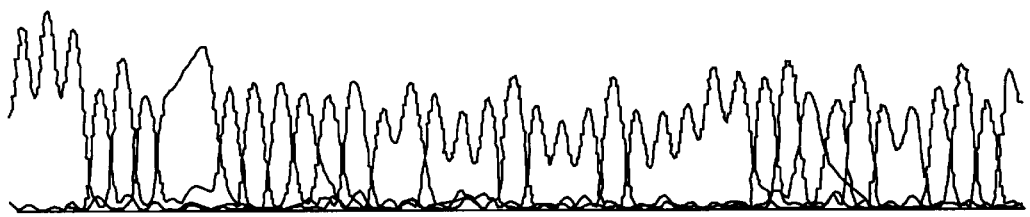
Figure 3C:
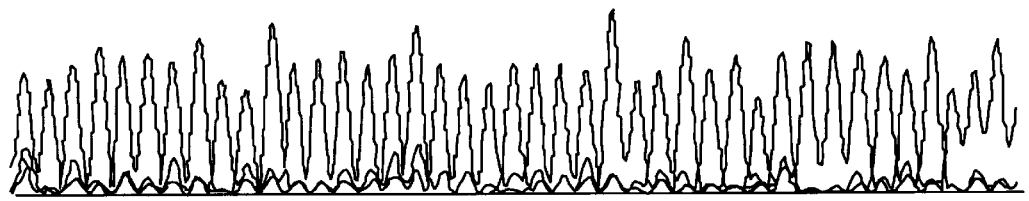
Figure 3D:
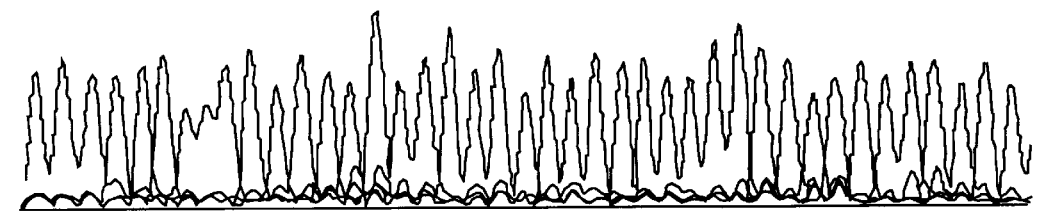

FIG. 3 illustrates the sequences obtained from the products amplified by the primer combinations 19F with 19R (standard PCR) and 19XF with 19R (opposite strand joining PCR). Electropherograms A and B (FIGS. 3A and 3B) represent the sequence in both directions for the products (FIGS. 2B, 2D, 2E and 2F) amplified by the primers 19XF and 19R and sequenced with the −28M13 reverse primer in a single reaction and in a single lane on a sequencing gel. Electropherograms C and D (FIGS. 3C and 3D) represent the sequence of the two strands for the product amplified by the primers 19F and 19R and sequenced with the −40M13 forward or the −28M13 reverse primer in two separate reactions and in two lanes on a sequencing gel. Comparison of the electropherograms A and C shows the same sequence for the products generated by primers 19XF with 19R and for the product generated by the primers 19F with 19R sequenced by the same sequencing primer. Comparison of the electropherograms B and D shows the same sequence for the products generated by primers 19XF with 19R and for the product generated by primers 19F with 19R but sequenced by two different sequencing primers. Thus, from electropherograms A and B, the sequence of exon 19 of the BRCA1 gene can be read in both directions from a single set of sequencing reactions using only one sequencing primer.

In tests to optimize the above method of opposite strand joining PCR, various concentrations (0.0125 $\mu$M, 0.025 $\mu$M, 0.05 $\mu$M, 0.1 $\mu$M, 0.2 $\mu$M and 0.4 $\mu$M) of the opposite strand joining primer, 19XF, in combination with various lengths (20 bases, 14 bases, 10 bases, 9 bases, 8 bases and 6 bases) of the 5' reverse complemented sequence while keeping the concentration of the primer 19R at 0.1 $\mu$M. Equal sequence signal intensity values for both directions in the turnaround product were seen when the length of the 5' reverse complemented sequence in the 19XF primer was 9 bases and the concentration was 0.4 $\mu$M.

Those of skill in the art will realize that the Example is only illustrative and that many variations of the specific methods of the Example are possible. For example, one could perform a PCR reaction which adds the oligomers at the ends of the genomic DNA to produce the structures shown in FIGS. 2E and 2F. These products can then be sequenced with a single primer by means other than discussed in the Example. It is not necessary to use fluorescently labeled primers, radioactively labeled primers can be used instead, and it is unnecessary to perform cycle sequencing, rather ordinary sequencing methods without cycling may be utilized. Similarly, there is no need to use the M13 sequences as part of the primers as used in the Example. This could be replaced by any other known sequence of DNA. Any gene sequence can be analyzed in this manner and the use of BRCA1 or BRCA2 was merely intended to be illustrative. These variations and other variations will be obvious to one of skill in the art and the disclosure is meant to be exemplary only and not inclusive of the means of performing the invention.

LIST OF REFERENCES

Chadwick, R. B., M. P. Conrad, M. D. McGinnis, L. Johnston-Dow, S. L. Spurgeon and M. N. Kronick (1996). "Heterozygote and Mutation Detection by Direct Automated Fluorescent DNA Sequencing Using a Mutant Taq DNA Polymerase." BioTechniques 20: 676–683.

Compton, J. (1991). "Nucleic acid sequence-based amplification." Nature 350: 91–92.

Fahy, E., D. Y. Kwoh and T. R. Gingeras (1991). "Self-sustained sequence replication (3SR): an isothermal transcription-based amplification system alternative to PCR." PCR Methods Appl. 1: 25–33.

Fischer, S. G. and L. S. Lerman (1983). "DNA fragments differing by single base pair substitutions separated in denaturing gradient gels: Correspondence with melting theory." Proc. Natl. Acad. Sci. USA 80: 1579–1583.

Jones, D. H. and S. C. Winistorfer (1992). "Sequence specific generation of a DNA panhandle permits PCR amplification of unknown flanking DNA." Nucl. Acids. Res. 30: 595–600.

Ju, J., I. Kheterpal, J. R. Scherer, C. W. Fuller, A. N. Glazer and R. A. Mathies (1995a). "Design and synthesis of fluorescence energy transfer dye labeled primers and their application for DNA sequencing and analysis." Annals of Biochemistry 231: 131–140.

Ju, J., C. Ruan, C. W. Fuller, A. N. Glazer and R. A. Mathies (1995b). "Fluorescence energy transfer dye labeled primers for DNA sequencing and analysis." Proc. Natl. Acad. Sci USA 92: 4347–4351.

Kalman, L. V., R. D. Abranson and D. H. Gelfand (1995). "Thermostable DNA polymerases with altered discrimination properties." Genome Science Technology 1: 42.

Maxam, A. M. and W. Gilbert (1977). "A new method for sequencing DNA." Proc. Natl. Acad. Sci. USA 74: 560–564.

Myers, R. M., S. G. Fisher, T. Maniatis and L. S. Lerman (1985a). "Modification of the melting properties of duplex DNA by attachment of a GC-rich sequence as determined by denaturing gradient gel electrophoresis." Nucl. Acids Res. 13: 3111–3129.

Myers, R. M., S. G. Fisher, L. S. Lerman and T. Maniatis (1985b). "Nearly all single base substitutions in DNA fragments joined to GC-clamp can be detected by denaturing gradient gel electrophoresis. Nucl. Acids Res. 13: 3131–3145.

Sanger, F., S. Nicklen and A. R. Coulson (1977). "DNA sequencing with chain-terminating inhibitors." Proc. Natl. Acad Sci. 74: 5463–5467.

Spargo, C. A., M. S. Fraiser, M. van Cleve, D. J. Wright, C. M. Nycz, P. A. Spears and G. T. Walker (1996). "Detection of M. tuberculosis DNA using thermophilic strand displacement amplification." Mol Cell. Probes 10: 247–256.

Tabor, S. and C. C. Richardson (1995). "A single residue in DNA polymerases of the Escherichia coli DNA polymerase I family is critical for distinguishing between deoxy- and dideoxyribonucleotides." Proc. Natl. Acad. Sci. USA 92: 6339–6343.

Walker, G. T. (1995). "Strand Displacement Amplification." U.S. Pat. No. 5,455,166.

Walker, G. T., M. S. Fraiser, J. L. Schram, M. C. Little, J. G. Nadeau and D. P. Malinowski (1992). "Strand displacement amplification—an isothermal, in vitro DNA amplification technique." *Nucl. Acids Res.* 20: 1691–1696.

Wu, D. Y. and R. B. Wallace (1989). "The ligation amplification reaction (LAR) amplification of specific DNA sequences using sequential rounds of template-dependent ligation." *Genomics* 4: 560–569.

---

What is claimed is:

1. A method for sequencing both strands of a double-stranded DNA molecule in a single set of sequencing reactions using a sequencing primer of a single nucleotide sequence wherein said method comprises the steps of:
   a) amplifying said double-stranded DNA molecule using a pair of amplification primers to form amplified DNA wherein each strand of said amplified DNA comprises a first region and a second region wherein said first region and said second region are reverse complements of each other;
   b) denaturing said amplified DNA to form single strands of DNA;
   c) allowing intrastrand-annealing of said single strands of DNA wherein said first region on one strand of DNA anneals with said second region on said one strand of DNA to form intrastrand-annealed DNA;
   d) extending said intrastrand-annealed DNA to yield panhandle DNA which upon denaturation yields a single-stranded DNA molecule comprising sequence of said both strands of double-stranded DNA; and
   e) sequencing said single-stranded DNA using said sequencing primer to obtain sequence data,
   wherein said sequence data comprises sequence for both strands of said double-stranded DNA molecule.

2. The method of claim 1 wherein following step (d) the method comprises the steps of:
   (e) amplifying said panhandle DNA to form a second amplified DNA; and
   (f) sequencing said second amplified DNA of step (e) using said sequencing primer to obtain sequence data,
   wherein said sequence data comprises sequence for both strands of said double-stranded DNA molecule.

3. The method of claim 1 wherein said sequencing is performed by cycle sequencing.

4. The method of claim 2 wherein said sequencing is performed by cycle sequencing.

5. The method of claim 1 wherein said amplifying is performed by a method selected from the group consisting of polymerase chain reaction, strand displacement amplification, thermophilic strand displacement amplification, self-sustained sequence replication, and nucleic acid sequence-based amplification (NASBA).

6. The method of claim 2 wherein said amplifying is performed by a method selected from the group consisting of polymerase chain reaction, strand displacement amplification, thermophilic strand displacement amplification, self-sustained sequence replication, and NASBA.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:1:

AGGAAACAGC TATGACCATT GATCCTCATT ATCATGGAAA ATTTGT        46

(2) INFORMATION FOR SEQ ID NO:2:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:2:

GTTTTCCCAG TCACGACGGT CATTCTTCCT GTGCTCTTTT GT        42

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

CAGCGATTCG TCATTCTTCC TGTGCTCTTT TGT        33

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:4:

TCCTCTGTCA TTCTTCCTGT GCTCTTTTGT GAATCGCTGA CCTCT        45